United States Patent [19]

Steele et al.

[11] Patent Number: 5,106,754
[45] Date of Patent: Apr. 21, 1992

[54] ZERO GRAVITY COMPATIBLE TOTAL ORGANIC AND INORGANIC CARBON ANALYZER

[75] Inventors: John W. Steele, Torrington; Philip J. Birbara, Windsor Locks; Timothy A. Nalette, Tolland, all of Conn.

[73] Assignee: United Technologies Corporation, Hartford, Conn.

[21] Appl. No.: 544,767

[22] Filed: Jun. 27, 1990

[51] Int. Cl.$^5$ ............................................. G01N 21/00
[52] U.S. Cl. ...................................... 436/146; 436/178; 436/150; 436/160; 436/161; 422/89; 422/93; 73/23.41
[58] Field of Search .................... 422/89, 93; 436/177, 436/178, 139, 140, 141, 158, 160, 161, 162, 145, 146; 73/23.41

[56] References Cited

U.S. PATENT DOCUMENTS

| | | | |
|---|---|---|---|
| 4,095,951 | 6/1978 | DiCola et al. | 436/146 |
| 4,288,229 | 9/1981 | Mar | 23/230 PC |
| 4,751,189 | 6/1988 | Rocklin | 436/150 |
| 4,794,088 | 12/1988 | Miyaki et al. | 436/161 |
| 4,819,478 | 4/1989 | Melcher | 73/61.1 C |
| 4,837,161 | 6/1989 | Stevens et al. | 436/52 |

Primary Examiner—Robert J. Hill, Jr.
Assistant Examiner—Abanti B. Singla
Attorney, Agent, or Firm—Alan C. Cohen; Pamela J. Mercier

[57] ABSTRACT

Total organic carbon (TOC) and inorganic carbon (TIC) monitoring of water is useful in determining the water quality. Conventional TOC and TIC monitoring techniques are not zero gravity compatible. The addition of microporous hydrophobic bladders in combination with a non-dispersive infrared analyzer allow for a two phase, liquid and gas, zero gravity compatible TOC monitoring technique. The non-dispersive infrared analyzer determines the quantity of carbon dioxide present in an aqueous sample after addition of acid and post oxidation. The measured carbon dioxide quantities derived from the aqueous sample are related to the TIC and TOC present in the aqueous sample, respectively.

39 Claims, 1 Drawing Sheet

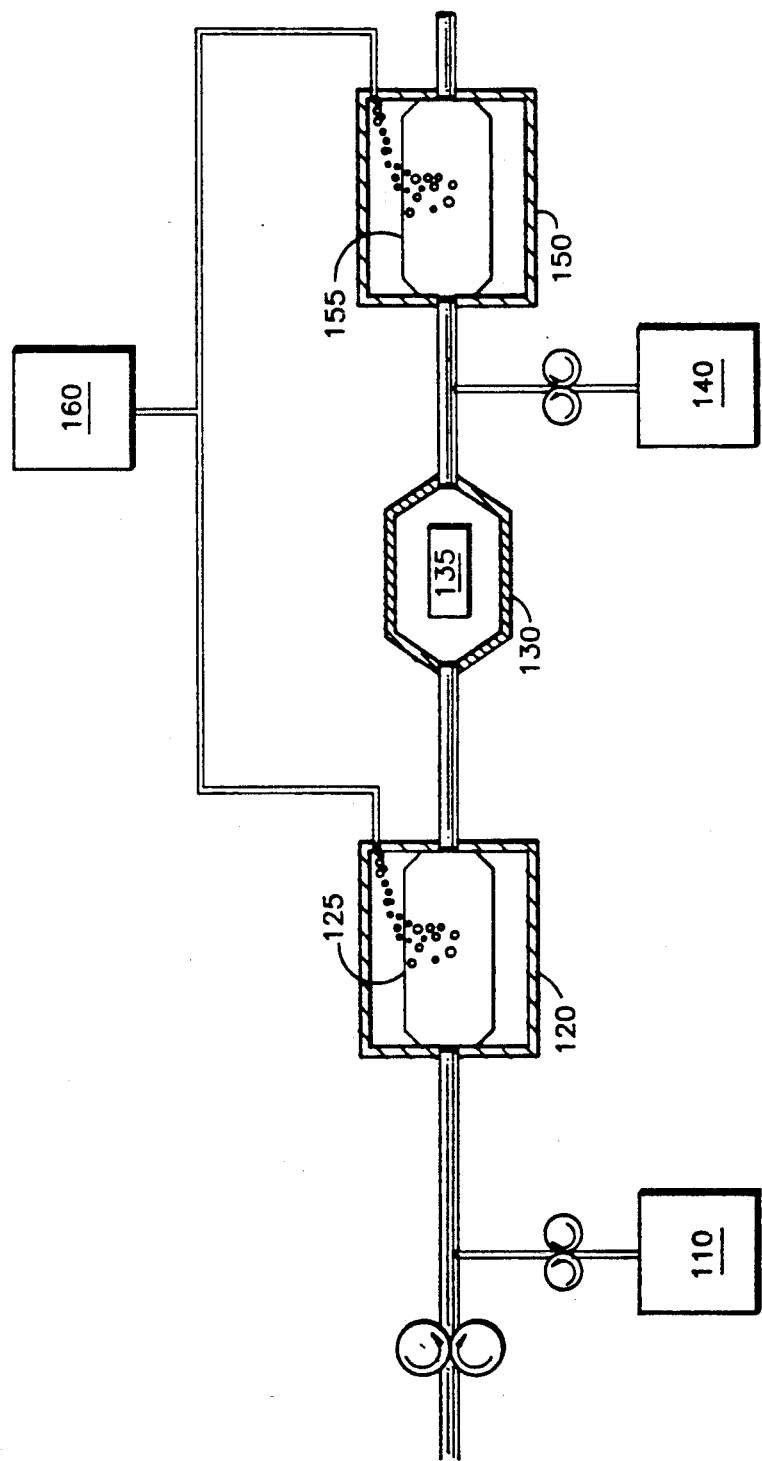

ZERO GRAVITY COMPATIBLE TOTAL ORGANIC AND INORGANIC CARBON ANALYZER

This application relates to copending, U.S. patent application Ser. No. 07/544,766, for TOTAL ORGANIC HALOGEN ANALYZER, filed on June 27, 1990; U.S. patent application Ser. No. 07/544,764, for AUTOMATED BIOLUMINESCENCE MICROBIAL MONITOR, filed June 27, 1990; U.S. patent application Ser. No. 07/544,763, for ZERO GRAVITY PURGE AND TRAP FOR MONITORING VOLATILE ORGANIC COMPOUNDS, filed June 27, 1990; U.S. patent application Ser. No. 07/544,765, for AN ELUANT AND PREPARATION APPARATUS AND METHOD FOR USING THE SAME, filed June 27, 1990 and U.S. patent application Ser. No. 07/544,768, for ZERO GRAVITY COMPATIBLE TOTAL ORGANIC AND INORGANIC CARBON ANALYZER, filed June 27, 1990, all commonly assigned.

TECHNICAL FIELD

This invention relates to a carbon analyzer, and especially to a zero gravity compatible total organic and inorganic carbon analyzer capable of detecting the quantity of organic and inorganic carbon present in an aqueous solution.

BACKGROUND ART

Water quality monitoring is necessary in many fields for numerous applications, especially if the water is to be used in applications requiring ultra pure water, such as water for the processing of semiconductor chips, coolant water for the nuclear power industry, and water used in pharmaceutical products.

One conventional means for assessing water quality is a total organic carbon (TOC) and a total inorganic carbon (TIC) analysis. This analytical procedure requires adjusting the aqueous sample pH to below 3 in order to convert major sources of inorganic carbon, carbonate and bicarbonate ions, to carbon dioxide. The carbon dioxide is purged from the sample with an inert gas, dried, and sent to a calibrated non-dispersive infrared analyzer (NDIR) for carbon dioxide analysis. The total inorganic carbon in the aqueous sample is related to the carbon dioxide content which is measured by the NDIR analyzer.

Once the inorganic carbon has been removed from the sample, the organic carbon is oxidized in the presence of an oxidant and UV radiation, again forming carbon dioxide. The carbon dioxide, as with the TIC carbon dioxide is purged, dried, and measured by the NDIR analyzer.

This process, although effective, is incapable of operating in a zero gravity environment (hereafter referred to as zero gravity compatibility) due to the presence of the two phases, liquid and gas. Therefore, what is needed in the art is a zero gravity compatible total organic and inorganic carbon analysis process and apparatus.

DISCLOSURE OF INVENTION

The present invention is an apparatus for total organic and inorganic carbon analysis and a process for determining these amounts. The apparatus utilizes a non-dispersive infrared analyzer, one or more microporous hydrophobic bladders, one or more containment vessels, an oxidation chamber, one or more means for purging, and a means for supplying oxidant.

Carbon dioxide, produced from the conversion of inorganic compounds in an aqueous sample, is purged from the aqueous sample in a first microporous hydrophobic bladder. Organic carbon in the aqueous sample is then oxidized to produce carbon dioxide. The oxidized aqueous sample enters a second microporous hydrophobic bladder. A second purge liberates the oxidation derived carbon dioxide which then permeates the bladder forming a gas stream. The gas stream containing the liberated oxidation derived carbon dioxide is analyzed in the non-dispersive infrared analyzer to determine the amount of organic carbon present in the aqueous sample. The total inorganic carbon can be determined by analyzing the carbon dioxide produced from the inorganic compounds in the aqueous sample in the non-dispersive infrared analyzer. The total carbon present in the aqueous sample can be determined by combining the amount of total inorganic carbon with the amount of total organic carbon.

The foregoing and other features and advantages of the present invention will become more apparent from the following description and accompanying drawing.

BRIEF DESCRIPTION OF DRAWINGS

The FIGURE is a schematic of a possible embodiment of the non-dispersive infrared analyzer for determining the total organic carbon and inorganic carbon content of an aqueous stream within a zero gravity environment.

BEST MODE FOR CARRYING OUT THE INVENTION

This invention discloses a total organic and inorganic carbon analyzer. This analyzer, a non-dispersive infrared analyzer, is capable of operating in a zero gravity environment.

Referring to the Figure, which is meant to be exemplary not limiting, the apparatus is comprised of a means for supplying acid (110), a microporous hydrophobic bladder (125) located within a gas containment vessel (120), and a second microporous hydrophobic bladder (155) located within a second gas containment vessel (150), an oxidation chamber (130), a means for supplying oxidant (140), and an NDIR analyzer (160).

Acid, which is introduced to an aqueous sample, adjusts the pH of the aqueous sample to less than about 3.0, converting the inorganic compounds in the sample, such as carbonate and bicarbonate, to carbon dioxide. The acid can be introduced to the aqueous sample within the first microporous hydrophobic bladder (125) or before it enters the first microporous hydrophobic bladder (125). The acid can be any means for converting inorganic compounds to carbon dioxide which does not adversely affect the NDIR analyzer or the test results, such as acids including sulfuric acid and phosphoric acid, can be used.

Once within the microporous hydrophobic bladder (125), a purge liberates the carbon dioxide (driving it into the gas phase), allowing it to permeate the microporous hydrophobic bladder (125). The purge frees the aqueous sample of the inorganic compounds, now carbon dioxide, allowing the sample to be tested for organic carbon. Any means for purging conventionally known in the art can be used, with an inert gas purge preferred. Inert gases typically used for this process include argon, nitrogen, and helium, although it is possible to utilize neon, krypton, xenon, and mixtures thereof.

The microporous hydrophobic bladder, an expandable/collapsible membrane which allows gas permeation, has a pore size between about 0.10 and about 2.0 microns, with between about 0.15 microns and about 0.50 microns preferred, and about 0.2 microns especially preferred. The bladder allows the separating of the liquid and gas phases, so as to render this process zero gravity compatible. Therefore, any means conventionally known in the art which allows gas permeation and is zero gravity compatible can be used. Note, however, the bladder can not contain any void spaces. Therefore, prior to the aqueous sample entering the bladder, the bladder is fully collapsed. As the aqueous sample and acid enter the bladder, it expands enough to accommodate these substances. The gas containment vessel (120) receives the carbon dioxide and inert gas which permeate the microporous hydrophobic bladder (125). The gas containment vessel (120), therefore, should be gas tight and larger than the fully expanded microporous hydrophobic bladder (125) to ensure unrestricted gas permeation.

The carbon dioxide and inert gas which has permeated the first microporous hydrophobic bladder (125) can be analyzed in the NDIR analyzer (160) to determine the TIC of the aqueous sample or can be discharged from the system. The TIC of the aqueous sample is needed if the total carbon in the aqueous sample is to be determined.

Once the inorganic compounds have been removed from the aqueous sample, the sample passes to the oxidation chamber (130). Within the oxidation chamber (130), the organic compounds in the aqueous sample are oxidized to form carbon dioxide. Any means for oxidizing organic compounds which is conventionally known in the art can be used, such as an oxidant, UV radiation, and combinations thereof. The embodiment of the present invention shown in the Figure is a combination of UV radiation (135) within the oxidation chamber followed by the addition of an oxidant. The UV radiation (135) can be produced by any means conventionally known in the art, such as mercury vapor (UV) lamps and bulbs of various frequencies in the ultraviolet region of the spectrum. The oxidant can be any oxidant capable of oxidizing organic compounds to form carbon dioxide. Typical oxidants include potassium persulfate and sodium dichromate.

After oxidation of the organic compounds, the aqueous sample enters the second microporous hydrophobic bladder (155) contained within the second gas containment vessel (150). The aqueous sample is again purged as described above, liberating the oxidation derived carbon dioxide. The inert gas together with the liberated oxidation derived carbon dioxide permeate the second microporous hydrophobic bladder (155), forming a gas stream. The gas stream is then analyzed in the NDIR analyzer (160). The second microporous hydrophobic bladder (155) and the second gas containment vessel (150) are similar in function and design to the first microporous hydrophobic bladder (125) and first gas containment vessel (120) described above.

Similarly, total carbon (TC) analysis is a summation of TIC and TOC analysis. This analysis involves converting the inorganic compounds, typically carbonates and bicarbonates, in an aqueous sample to carbon dioxide. The carbon dioxide is liberated with a purge within the first microporous hydrophobic bladder (125). Once in the gas phase the liberated carbon dioxide and inert gas permeate the first microporous hydrophobic bladder (125), moving into the gas containment vessel (120). The inert gas then transports the carbon dioxide to the NDIR to determine the carbon dioxide content which is related to the TIC.

The organic compounds in the purged aqueous sample are then oxidized within the oxidation chamber (130) to produce carbon dioxide. The oxidized aqueous sample then passes into a second microporous hydrophobic bladder (155) within a second gas containment vessel (150). The oxidation derived carbon dioxide is liberated via a purge. The inert gas and liberated oxidation derived carbon dioxide, the gas stream, permeate the microporous hydrophobic bladder (155). This gas stream is then routed to the NDIR to determine the liberated oxidation derived carbon dioxide content which is related to the TOC. The TC content of the aqueous sample can then be determined by adding the TIC and the TOC.

This approach is zero gravity compatible, an improvement over the prior art. Additionally, the apparatus is capable of complete automation.

Although this invention has been shown and described with respect to detailed embodiments thereof, it will be understood by those skilled in the art that various changes in form and detail thereof may be made without departing from the spirit and scope of the claimed invention.

We claim:

1. An apparatus for organic carbon analysis of an aqueous sample which comprises:

a. at least one gas containment vessel;
   b. at least one first microporous hydrophobic bladder;
   c. a means for supplying a first, reactive, carbon dioxide forming liquid;
   d. a first means for purging;
   e. an oxidation chamber constructed so as to oxidize any organic compounds present in said aqueous sample;
   f. at least one second gas containment vessel;
   g. at least one second microporous hydrophobic bladder;
   h. a second means for purging;
   i. a non-dispersive infrared analyzer constructed so as to analyze carbon dioxide derived from said oxidized aqueous sample; and
   j. a means for supplying an aqueous sample;

wherein said at least one first microporous hydrophobic bladder is located within said at least one first gas containment vessel, said means for supplying a first liquid is in flow communication with said at least one first microporous hydrophobic bladder and said means for supplying an aqueous sample so as to contact said first liquid with said aqueous sample and convert any inorganic compounds in said aqueous sample to carbon dioxide;

wherein said at least one first microporous hydrophobic bladder is further constructed so as to expand to a volume commensurate with and said aqueous sample present in said at least one first microporous hydrophobic bladder;

wherein said first means for purging is in flow communication with said at least one first microporous hydrophobic bladder said first means for purging constructed so as to purge any carbon dioxide formed, said first means for purging further being in flow communication with said non-dispersive infrared analyzer;

wherein said oxidation chamber is in flow communication with said at least one first microporous hydrophobic bladder, said oxidation chamber constructed so as to receive said aqueous sample from said at least one first microporous hydrophobic bladder;

wherein said at least one second microporous hydrophobic bladder is located within said at least one second gas containment vessel, said least one second microporous hydrophobic bladder is in flow communication with said oxidation chamber and is constructed so as to receive said oxidized aqueous sample from said oxidation chamber;

wherein said at least one second microporous hydrophobic bladder is constructed so as to expand to a volume commensurate with a volume of said oxidized aqueous sample present in said at least one second microporous hydrophobic bladder;

wherein said second means for purging is in flow communication with said at least one second microporous hydrophobic bladder, so as to purge said any carbon dioxide formed from said oxidized aqueous sample, said second means for purging is in flow communication with said non-dispersive infrared analyzer;

wherein said apparatus is zero gravity compatible and the quantity of organic carbon present in said aqueous sample is determined from the oxidation derived carbon dioxide in said aqueous sample.

2. An apparatus as in claim 1 wherein said at least one first microporous hydrophobic bladder and said at least one second microporous hydrophobic bladders have a pore size between about 0.10 micron and about 2.0 microns.

3. An apparatus as in claim 1 wherein the at least one second microporous hydrophobic bladder is the same as the at least one first microporous hydrophobic bladder.

4. An apparatus as in claim 1 wherein the second means for purging is the same as the first means for purging.

5. An apparatus as in claim 1 wherein the first and second means for purging comprise an inert gas purge.

6. An apparatus as in claim 5 wherein the inert gas is selected from the group consisting of argon, nitrogen, helium, neon, krypton, xenon, and mixtures thereof.

7. An apparatus for inorganic carbon analysis of an aqueous sample comprising said apparatus using an inert gas and an acid, which comprises:
   a. at least one gas containment vessel;
   b. at least one first microporous hydrophobic bladder;
   c. a means for supplying a reactive, carbon dioxide forming liquid which reacts with any inorganic carbon in the aqueous sample to form carbon dioxide;
   d. a means for purging any carbon dioxide; and
   e. a non-dispersive infrared analyzer constructed so as to analyze any carbon dioxide formed from said aqueous sample;
   wherein said at least one first microporous hydrophobic bladder is located within said at least one gas containment vessel, said first bladder constructed so as to expand to a volume commensurate with a volume of said liquid and said aqueous sample contacting said bladder;
   wherein said means for purging is in flow communication with said first bladder and said means for supplying a liquid, said means for purging constructed so as to purge said any carbon dioxide formed when said any inorganic compounds in said aqueous sample are contacted with said liquid,
   wherein said non-dispersive infrared analyzer is in flow communication with said first bladder, said analyzer further constructed so as to determine quantity of inorganic carbon present in said aqueous sample,
   wherein said apparatus is constructed to be zero-gravity compatible.

8. An apparatus as in claim 7 wherein the means for purging comprises an inert gas.

9. An apparatus as in claim 8 wherein the inert gas is selected from the group consisting of argon, nitrogen, helium, neon, krypton, xenon, and mixtures thereof.

10. An apparatus as in claim 7 wherein said at least one microporous hydrophobic bladder have a pore size between about 0.10 micron and about 2.0 microns.

11. An apparatus for total carbon analysis of an aqueous sample, which comprises:
   a. at least one gas containment vessel;
   b. at least one first microporous hydrophobic bladder;
   c. a means for supplying a first liquid, said first liquid having a volume;
   d. a first means for purging;
   e. an oxidation chamber constructed so as to oxidize any organic compounds in said aqueous sample;
   f. at least one second gas containment vessel;
   g. at least one second microporous hydrophobic bladder;
   h. a second means for purging;
   i. a non-dispersive infrared analyzer;
   j. a means for supplying an aqueous sample, said aqueous sample having a volume;
   wherein said at least one first microporous hydrophobic bladder is located within said at least one first gas containment vessel, said means for supplying a first liquid is in flow communication with said at least one first microporous hydrophobic bladder and said means for supplying an aqueous sample, so as to contact the first liquid with the aqueous sample and convert any inorganic compounds in said aqueous sample to carbon dioxide;
   wherein said at least one first microporous hydrophobic bladder is further constructed so as to expand to a volume commensurate with the volumes of said first liquid and said aqueous sample present in said at least one first microporous hydrophobic bladder,
   wherein said first means for purging is in flow communication with said at least one first microporous hydrophobic bladder, said first means for purging constructed so as to purge any carbon dioxide formed, said first means for purging further being in flow communication with said non-dispersive infrared analyzer;
   wherein said oxidation chamber is in flow communication with said at least one first microporous hydrophobic bladder so as to receive said aqueous sample from said at least one first microporous hydrophobic bladder;
   wherein said at least one second microporous hydrophobic bladder is located within said at least one second gas containment vessel, said at least one second microporous hydrophobic bladder is in flow communication with said oxidation chamber so as to receive said oxidized aqueous sample from said oxidation chamber;

wherein said at least one second microporous hydrophobic bladder is constructed so as to expand to a volume commensurate with a volume of said oxidized aqueous sample present in said at least one second microporous hydrophobic bladder;

wherein said second means for purging is in flow communication with said at least one second microporous hydrophobic bladder so as to purge any carbon dioxide formed from said oxidized aqueous sample, said second means for purging in flow communication with said non-dispersive infrared analyzer;

wherein said non-dispersive infrared analyzer is constructed so as to analyze carbon dioxide produced from said any inorganic compounds and oxidation derived carbon dioxide;

wherein said apparatus is zero-gravity compatible.

12. An apparatus as in claim 11 wherein the at least one first microporous hydrophobic bladder and the at least one second microporous hydrophobic bladder have a pore size between about 0.10 micron and about 2.0 microns.

13. An apparatus as in claim 11 wherein the at least one second microporous hydrophobic bladder is the same as the at least one first microporous hydrophobic bladder.

14. An apparatus as in claim 11 wherein the second means for purging is the same as the first means for purging.

15. An apparatus as in claim 11 wherein the first and second means for purging comprise an inert gas purge.

16. An apparatus as in claim 15 wherein the inert gas is selected from the group consisting of argon, nitrogen, helium, neon, krypton, xenon, and mixtures thereof.

17. A method for monitoring organic carbon in an aqueous sample which is zero gravity compatible, which comprises:
a. purging an aqueous sample located within a first microporous hydrophobic bladder to liberate carbon dioxide produced from inorganic compounds present in the aqueous sample, wherein liberated carbon dioxide permeates the first microporous hydrophobic bladder;
b. oxidizing the purged aqueous sample to convert organic compounds to carbon dioxide;
c. introducing the oxidized aqueous sample into a second microporous hydrophobic bladder;
d. purging the oxidized aqueous sample to liberate the oxidation derived carbon dioxide, wherein liberated oxidation derived carbon dioxide permeates the second microporous hydrophobic bladder to form a gas stream; and
e. moving the gas stream into a non-dispersive infrared analyzer to determine the concentration of liberated oxidation derived carbon dioxide in the aqueous sample whereby the quantity of organic carbon present in the aqueous sample is determined from the carbon dioxide present in the aqueous sample.

18. A method as in claim 17 wherein the aqueous sample and the oxidized aqueous sample are purged with an inert gas.

19. A method as in claim 18 wherein the inert gas is selected from the group consisting of helium, nitrogen, argon, neon, krypton, xenon, and mixtures thereof.

20. A method as in claim 17 wherein the first and second microporous hydrophobic bladders have a pore size between about 0.10 microns and about 2.0 microns.

21. A method as in claim 17 wherein the organic compounds are oxidized with a means selected from the group consisting of an oxidizer and UV radiator, and combinations thereof.

22. A method as in claim 21 wherein the oxidizer means comprises an oxidant, wherein the oxidant is selected from the group consisting of potassium persulfate and sodium dichromate.

23. A method as in claim 21 wherein said radiator means is selected from the group consisting of ultraviolet lamps and bulbs having frequencies in the ultraviolet region of the spectrum 24. A method as in claim 17 wherein the first microporous hydrophobic bladder and the second microporous hydrophobic bladder are the same.

25. A method for monitoring inorganic carbon in an aqueous solution which is zero gravity compatible, which comprises:
a. purging an aqueous sample located within a microporous hydrophobic bladder to liberate carbon dioxide produced from inorganic compounds in the aqueous sample, wherein liberated carbon dioxide permeates the microporous hydrophobic bladder; and
b. analyzing the carbon dioxide in a non-dispersive infrared analyzer;

whereby the quantity of inorganic carbon present in the aqueous sample is determined from the carbon dioxide present in the aqueous sample.

26. A method as in claim 25 wherein the microporous hydrophobic bladder has a a pore size between about 0.10 microns and about 2.0 microns.

27. A method as in claim 25 wherein the carbon dioxide is produced when acid is added to the aqueous sample.

28. A method as in claim 27 wherein the acid is selected from the group consisting of sulfuric acid, phosphoric acid, and mixtures thereof.

29. A method as in claim 25 wherein the purging step comprises an inert gas.

30. A method as in claim 29 wherein the inert gas is selected from the group consisting of helium, nitrogen, argon, neon, krypton, xenon, and mixtures thereof.

31. A method for monitoring total carbon in an aqueous solution which is zero gravity compatible, which comprises:
a. purging an aqueous sample located within a first microporous hydrophobic bladder to liberate carbon dioxide produced from inorganic compounds in the aqueous sample, wherein liberated carbon dioxide permeates the microporous hydrophobic bladder;
b. analyzing the carbon dioxide in a non-dispersive infrared analyzer;
c. oxidizing the purged aqueous sample to convert organic compounds to carbon dioxide;
d. moving the oxidized aqueous sample into a second microporous hydrophobic bladder;
e. purging the oxidized aqueous sample to liberate the oxidation derived carbon dioxide, wherein liberated oxidation derived carbon dioxide permeates the second microporous hydrophobic bladder to form a gas stream; and
f. introducing the gas stream into a non-dispersive infrared analyzer to determine the concentration of liberated oxidation derived carbon dioxide in the aqueous sample;

whereby the total carbon present in the aqueous sample is determined from the carbon dioxide produced from the inorganic compounds and oxidation derived carbon dioxide present in the aqueous sample.

32. A method as in claim 31 wherein the microporous hydrophobic bladder has a pore size between about 0.10 microns and about 2.0 microns.

33. A method as in claim 31 wherein the carbon dioxide is produced by acid being added to the aqueous sample.

34. A method as in claim 33 wherein the acid is selected from the group consisting of sulfuric acid, phosphoric acid, and mixtures thereof.

35. A method as in claim 31 wherein the purging step comprises inert gas.

36. A method as in claim 35 wherein the inert gas is selected from the group consisting of helium, nitrogen, argon, neon, krypton, xenon, and mixtures thereof.

37. A method as in claim 31 wherein the organic compounds are oxidized with a means selected from the group consisting of an oxidizer, UV radiator, and combinations thereof.

38. A method as in claim 38 wherein the oxidizer comprises an oxidant, said oxidant is selected from the group consisting of potassium persulfate and sodium dichromate.

39. A method as in claim 37 wherein the UV radiators is ultraviolet selected from the group consisting of ultraviolet lamps and bulbs having frequencies in the ultraviolet region of the spectrum.

* * * * *